(12) United States Patent
Hwang et al.

(10) Patent No.: US 10,604,257 B2
(45) Date of Patent: Mar. 31, 2020

(54) UNMANNED AERIAL VEHICLE FOR AIR SAMPLING

(71) Applicant: INTERNATIONAL BUSINESS MACHINES CORPORATION, Armonk, NY (US)

(72) Inventors: Jinho Hwang, Ossining, NY (US); Clifford A. Pickover, Yorktown Heights, NY (US); Maja Vukovic, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 579 days.

(21) Appl. No.: 15/195,924

(22) Filed: Jun. 28, 2016

(65) Prior Publication Data

US 2017/0369168 A1 Dec. 28, 2017

(51) Int. Cl.
*B64D 1/16* (2006.01)
*B64D 1/18* (2006.01)
(Continued)

(52) U.S. Cl.
CPC ............... *B64D 1/18* (2013.01); *A61L 9/03* (2013.01); *A61L 9/14* (2013.01); *B64C 39/024* (2013.01);
(Continued)

(58) Field of Classification Search
CPC .......... B64D 1/16; B64D 1/18; B64C 39/024; B64C 2201/127; B64C 2201/108;
(Continued)

(56) References Cited

U.S. PATENT DOCUMENTS 9,176,104 B2 11/2015 Haddad et al.
9,405,533 B2 * 8/2016 Bouzas ............... G06F 7/00
(Continued)

FOREIGN PATENT DOCUMENTS

CN 203644359 U 6/2014
WO WO2004108173 A1 12/2004
(Continued)

OTHER PUBLICATIONS

Gomez-Marin, A. et al., "Active sampling and decision making in *Drosophila* chemotaxis," Nature Communications, Aug. 2011. (pp. 1-10).
(Continued)

*Primary Examiner* — Cuong H Nguyen
(74) *Attorney, Agent, or Firm* — Tutunjian & Bitetto, P.C.; Anthony Curro

(57) ABSTRACT

An unmanned aerial vehicle for scent analysis. The unmanned aerial vehicle includes a sensor array to sample ambient air in a location to detect an odor, a pattern recognition unit coupled to a database to identify the odor, wherein the odor is compared to identification information stored in the database, and a mapping unit to estimate an assessment value associated with the odor and to generate an instruction to one or more components of the unmanned aerial vehicle to perform a function when the assessment value exceeds a predetermined threshold value, wherein the function includes activating one or more feedback outputs on the unmanned aerial vehicle.

20 Claims, 7 Drawing Sheets

(51) Int. Cl.
*G01N 33/00* (2006.01)
*B64C 39/02* (2006.01)
*A61L 9/03* (2006.01)
*A61L 9/14* (2006.01)

(52) U.S. Cl.
CPC ..... *G01N 33/0001* (2013.01); *A61L 2209/111* (2013.01); *A61L 2209/12* (2013.01); *B64C 2201/027* (2013.01); *B64C 2201/108* (2013.01); *B64C 2201/12* (2013.01); *B64C 2201/127* (2013.01)

(58) Field of Classification Search
CPC . B64C 2201/027; B64C 2201/12; A61L 9/02; A61L 9/03; A61L 9/14; A61L 2209/11; A61L 2209/12
USPC .......................................... 701/3; 702/22–24
See application file for complete search history.

(56) References Cited

U.S. PATENT DOCUMENTS

| | | | |
|---|---|---|---|
| 2005/0112085 A1* | 5/2005 | MacDonald | A61F 13/42 424/76.1 |
| 2006/0114324 A1 | 6/2006 | Farmer et al. | |
| 2006/0191319 A1 | 8/2006 | Kurup | |
| 2007/0196319 A1* | 8/2007 | Alfrey | A01K 1/0152 424/76.2 |
| 2007/0241261 A1* | 10/2007 | Wendt | G01D 9/005 250/221 |
| 2009/0261987 A1* | 10/2009 | Sun | G01N 35/00732 340/870.07 |
| 2010/0004798 A1 | 1/2010 | Bodin et al. | |
| 2010/0022563 A1* | 1/2010 | Henkin | A61K 31/47 514/263.34 |
| 2012/0178768 A1* | 7/2012 | Henkin | A61K 31/522 514/263.34 |
| 2013/0236421 A1* | 9/2013 | Kodo | A61K 35/74 424/93.4 |
| 2013/0278427 A1* | 10/2013 | Setton | G08B 21/12 340/584 |
| 2015/0192437 A1* | 7/2015 | Bouzas | G06F 7/00 701/2 |
| 2015/0268210 A1* | 9/2015 | Cristoforo | G08B 21/14 702/24 |
| 2015/0274294 A1 | 10/2015 | Dahlstrom | |
| 2015/0287330 A1* | 10/2015 | Kron | G09B 23/28 434/219 |
| 2015/0332523 A1* | 11/2015 | Ranasinghe | H04W 24/10 701/34.2 |
| 2015/0344136 A1 | 12/2015 | Dahlstrom | |
| 2016/0059145 A1 | 3/2016 | Cortelyou et al. | |
| 2016/0232811 A9* | 8/2016 | Connor | G09B 5/00 |
| 2016/0325832 A1* | 11/2016 | Shukla | B64C 39/024 |
| 2016/0363339 A1* | 12/2016 | Blackley | A61L 9/032 |
| 2017/0003684 A1* | 1/2017 | Knudsen | G01N 21/51 |
| 2017/0042934 A1* | 2/2017 | Bastos | A61K 33/00 |
| 2017/0056594 A1* | 3/2017 | Chin | A61M 5/3129 |
| 2017/0227548 A1* | 8/2017 | Henkin | A61K 31/522 |
| 2017/0235308 A1* | 8/2017 | Gordon | G05D 1/0016 701/2 |

FOREIGN PATENT DOCUMENTS

| | | |
|---|---|---|
| WO | WO2007015657 A1 | 2/2007 |
| WO | WO2015105851 A1 | 7/2015 |

OTHER PUBLICATIONS

Sucker, K., et al., "Odor frequency and odor annoyance. Part I: assessment of frequency, intensity and hedonic tone of environmental odors in the field," International Archives of Occupational and Environmental Health, vol. 81, No. 6, May 2008. (pp. 1-12).

* cited by examiner

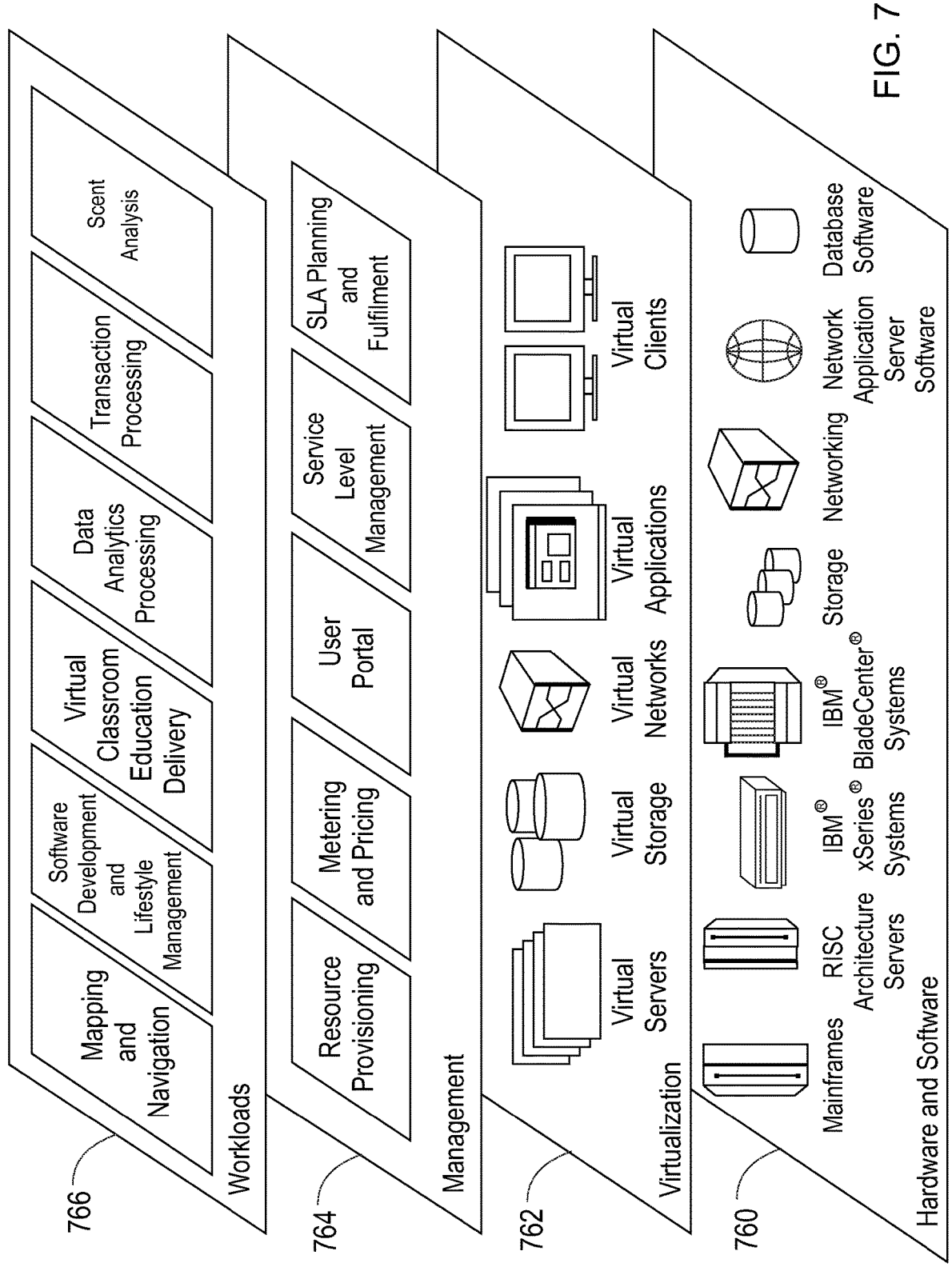

UNMANNED AERIAL VEHICLE FOR AIR SAMPLING

BACKGROUND

Technical Field

The present invention relates generally to an unmanned aerial vehicle and, in particular, to an unmanned aerial vehicle for providing scent analysis and distribution.

Description of the Related Art

Certain odors and/or chemical substances, which are typically sensed by sensory cells via olfaction, may be dispersed in various situations. For example, certain odors including pleasant and/or unpleasant scents may be distributed via ventilation systems in buildings to help individuals cope with claustrophobic effects, to lower decibel level, and/or to advertise products. These distribution mechanisms, however, include stationary devices. In many situations, it is desirable to detect and identify odors or the substances that cause them, and perform real-time classification of odors.

SUMMARY

According to an aspect of the present principles, an unmanned aerial vehicle for scent analysis is provided. The unmanned aerial vehicle may include a sensor array to sample ambient air in at least one location to detect at least one odor, a pattern recognition unit coupled to a database to identify the at least one odor, wherein the at least one odor is compared to identification information stored in the database, and a mapping unit to estimate an assessment value associated with the at least one odor and to generate an instruction to one or more components of the unmanned aerial vehicle to perform at least one function when the assessment value exceeds a predetermined threshold value, wherein the at least one function includes activating one or more feedback outputs on the unmanned aerial vehicle.

According to another aspect of the present principles, a method for scent analysis using an unmanned aerial vehicle is provided. The method may include sampling ambient air in at least one location to detect at least one odor, identifying, using a database, the at least one odor, wherein the at least one odor is compared to identification information stored in the database, estimating an assessment value associated with the at least one odor, and automatically performing at least one function when the assessment value exceeds a predetermined threshold value, wherein the at least one function includes activating one or more feedback outputs on the unmanned aerial vehicle.

According to another aspect of the present principles, a non-transitory computer readable storage medium for scent analysis using an unmanned aerial vehicle is provided. The non-transitory computer readable storage medium may include a computer readable program for scent analysis using an unmanned aerial vehicle, wherein the computer readable program, when executed on a computer, causes the computer to execute sampling ambient air in at least one location to detect at least one odor, identifying, using a database, the at least one odor, wherein the at least one odor is compared to identification information stored in the database, estimating an assessment value associated with the at least one odor, and automatically performing at least one function when the assessment value exceeds a predetermined threshold value, wherein the at least one function includes activating one or more feedback outputs on the unmanned aerial vehicle.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein:

FIG. 7 is a schematic diagram of exemplary abstraction model layers, in accordance with an embodiment of the present principles.

DETAILED DESCRIPTION

Figure 1:
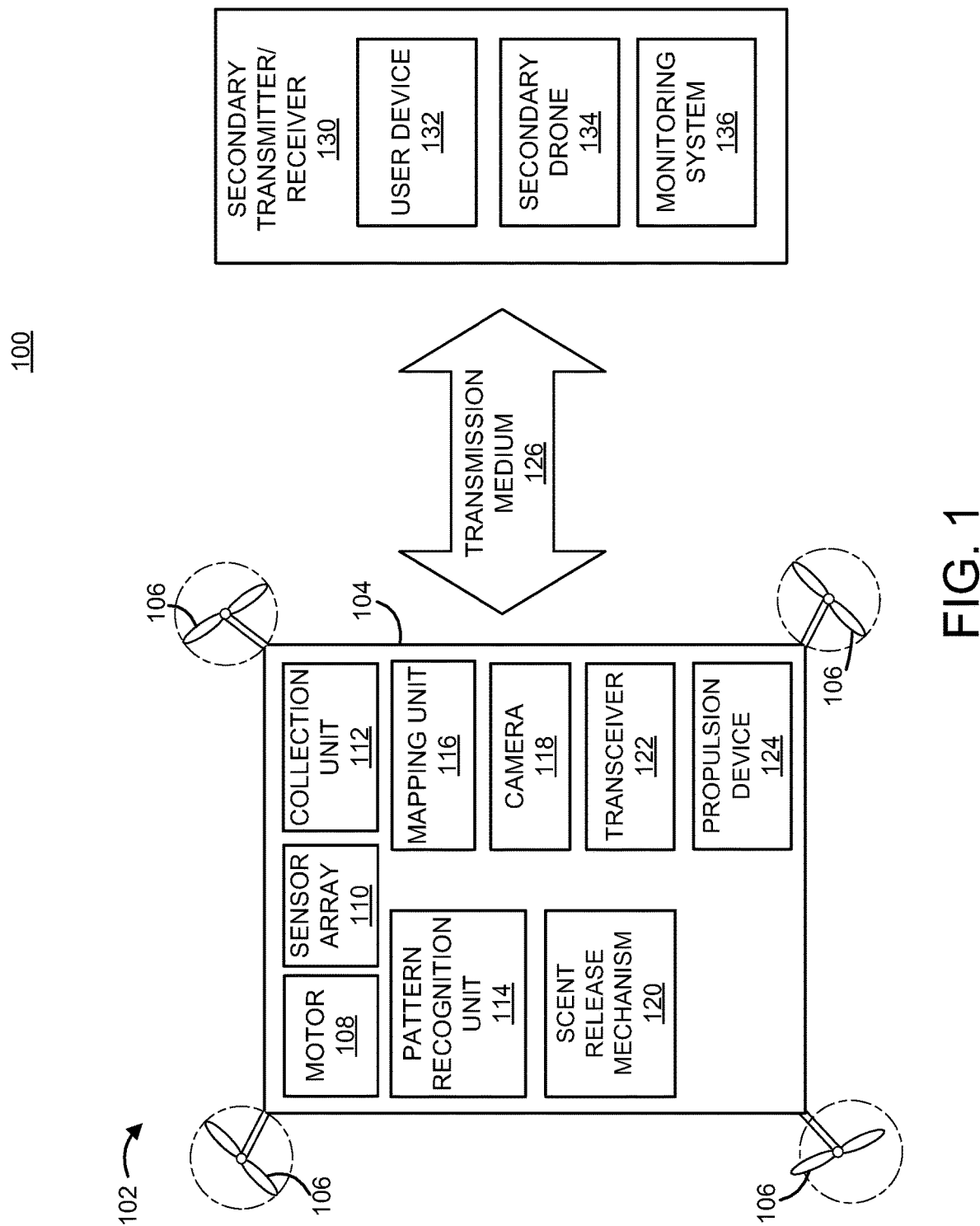
FIG. 1 is a block/flow diagram of an exemplary system for scent analysis using an unmanned aerial vehicle, in accordance with an embodiment of the present principles.

The present principles are directed to unmanned aerial vehicles for scent analysis and distribution. In some embodiments, the present principles provide systems, methods and computer program products to monitor and/or detect one or more scents in a particular area, perform scent analysis on the one or more scents, such as identify the scents and/or determine a level of pleasantness and/or unpleasantness of the scents, and disperse one or more scents based on such assessment. In some embodiments, the system, method and computer program product described herein may employ hedonic assessment to assess and/or scale odors based on pleasantness/unpleasantness, and/or computer-vision algorithms to identify a source of an odor and instruct a plurality of drones to disperse and/or distribute a scent in odor gradients.

It should be understood that the word "air sample", "odor" and/or "scent" is used loosely and is not intended to suggest any limitation as to the scope of use or functionality of embodiments of the present principles described herein. For example, "odor" and/or "scent" may be used interchangeably and may refer to, but is not limited to, any pleasant and/or unpleasant odors, scents, fragrances, aromas, etc. In some embodiments, the air sample may be odorless but may contain one or more chemical substances.

The present invention may be a system, a method and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring to the drawings in which like numerals represent the same or similar elements and initially to FIG. 1, an exemplary system 100 for providing scent analysis using an unmanned aerial vehicle 102 is illustratively depicted. It should be understood by one of ordinary skill in the art that the unmanned aerial vehicle 102 may comprise a drone, a drone-like unit, or a similarly functioning device. In some embodiments, the unmanned aerial vehicle 102 may be employed to monitor and/or assess one or more scents in a particular area and disperse a scent based on such assessment.

The unmanned aerial vehicle 102 may include a housing unit 104, at least one movement mechanism 106, and a motor 108. The components of the unmanned aerial vehicle 102 may be affixed on the outside of the housing unit 104, or alternatively, may be enclosed within the housing unit 104 of the unmanned aerial vehicle 102.

In some embodiments, the at least one movement mechanism 106 may include a single propeller, a plurality of propellers, a propulsion mechanism, or similarly functioning devices. In one embodiment, the at least one movement mechanism 106 may be powered by at least one motor 108 and a power supply (not shown) to provide movement for the unmanned aerial vehicle 102. The movement mechanism(s) 106 may be placed at any desired location on the unmanned aerial vehicle 102, such that the placement of the movement mechanism(s) 106 does not interfere with each other or with another component positioned on the unmanned aerial vehicle 102.

Figure 3:
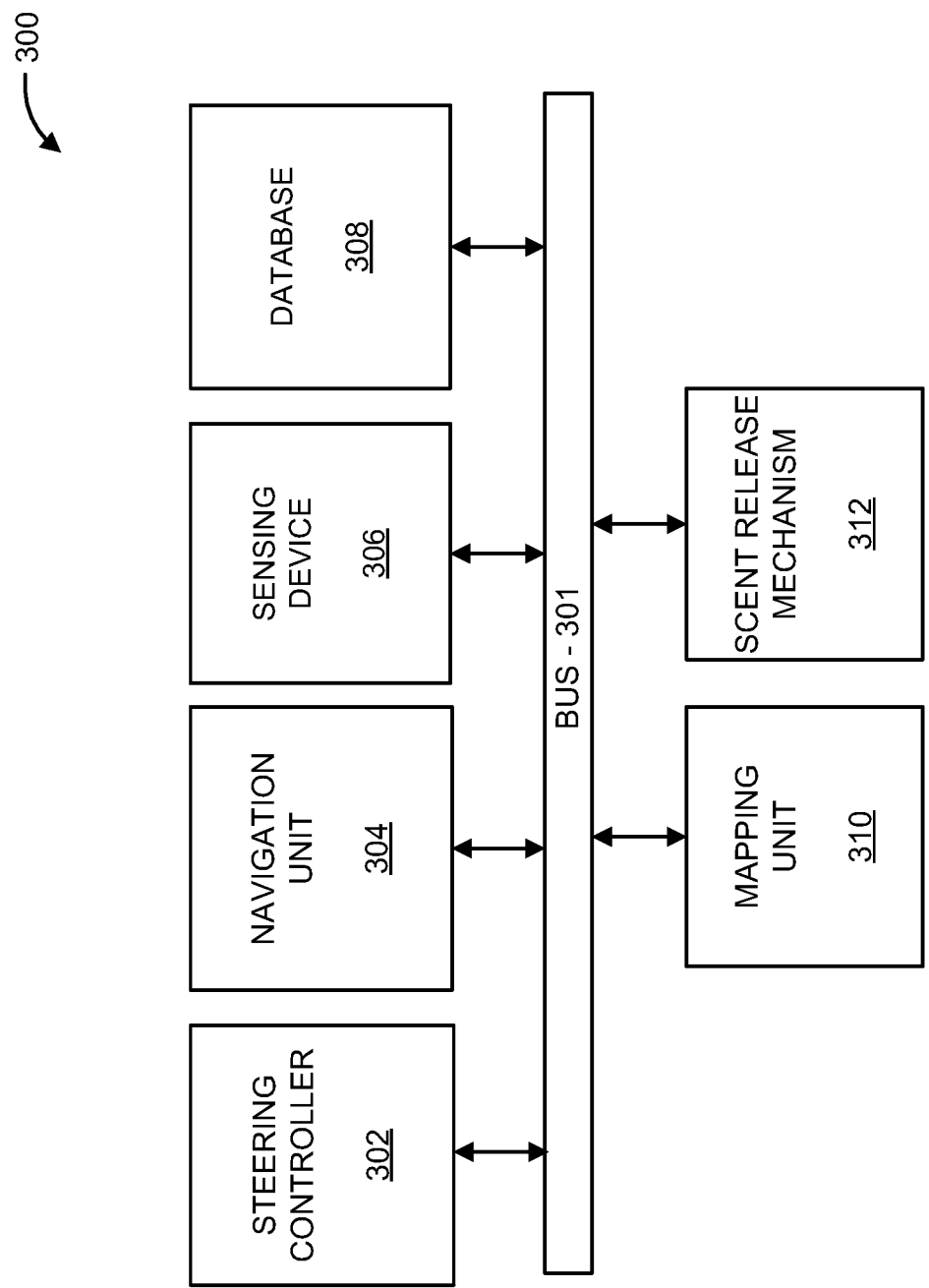
FIG. 3 is a block/flow diagram of an exemplary system for scent analysis using an unmanned aerial vehicle, in accordance with an embodiment of the present principles.

In one embodiment, the movement mechanism 106 and/or motor 108 provides aerial movement for the unmanned aerial vehicle 102 in multiple degrees of freedom. Multiple degrees of freedom generally refers to the ability for the unmanned aerial vehicle 102 to move in a three-dimensional space. Specifically, the movement mechanism 106 and/or motor 108 may be controlled by a steering controller 302, as illustrated in FIG. 3, to move the unmanned aerial vehicle 102 along three perpendicular axes, namely forward/backward movement, up/down movement, and left/right movement. In addition, the steering controller 302 may control the movement of the unmanned aerial vehicle in a 360 degree rotation, tilting forward/backward movement (e.g., pitching), swiveling left/right movement (e.g., yawing), and pivoting side to side movement (e.g., rolling).

In one embodiment, the movement mechanism(s) 106 and/or motor 108 provides movement for the unmanned aerial vehicle 102 to, for example, detect one or more odors/scents and/or move the unmanned aerial vehicle 102 toward the one or more scents to perform hedonic assessment and/or scent distribution. For example, the movement mechanisms 106 and/or motor 108 may provide movement for the unmanned aerial vehicle 102 to detect one or more scents in a particular location and/or disperse one or more scents within the particular location, as will be described in further detail below. In an embodiment, the movement mechanism(s) and/or motor 108 may provide movement for the unmanned aerial vehicle such that the unmanned aerial vehicle 102 may detect odor gradients in a particular location. An odor gradient may include, for example, one or more scents having varying magnitudes within a room, such as varying concentration levels. In further embodiments, the movement mechanism(s) 106 and/or motor 108 provides movement for the unmanned aerial vehicle 102 to avoid collision between the unmanned aerial vehicle 102 and an object, such as a person, a doorway, a building, and/or other structures.

In an embodiment, the unmanned aerial vehicle 102 may include a sensor array 110. The sensor array 110 may include one or more sensors, such as chemical sensors, acoustic sensors (e.g., microphone), infrared sensors, optical sensors, collision avoidance sensors (e.g., proximity sensors), heat sensors, etc. In an embodiment, the sensor array 110 may include one or more chemosensors (e.g., chemoreceptors) which may detect chemical stimuli and/or chemical substances in an environment. The sensory array 110 may monitor and/or sample ambient air in one or more locations to detect one or more odors and/or varying gradients of the one or more odors, such a change in concentration level of a particular odor.

The sensor array 110 may include a plurality of a same type of sensor or may include a plurality of different types of sensors. In an embodiment, the sensor array 110 may be configured to sample ambient air in a particular location and detect one or more odors within the particular location. For example, odors and/or scents may include one or more chemical compounds, chemical substances, and/or chemical structures. In addition, odors and/or scents may include perfume scents (e.g., floral, musty, minty, etc.), smell of food, fragrances, essential oils, pheromones, etc. In some embodiments, the scent(s) may be odorless but may still be associated with chemical compounds, such as carbon monoxide.

In an embodiment, the sensor array 110 may detect and/or identify a list of chemical compounds present in ambient air and/or output a chemical structure of the odor. For example, the sensory array 110 may employ chromatography (e.g., gas chromatography) to determine and/or detect certain chemical substances present in the ambient air and/or odor. Accordingly, the sensory array 110 may perform chemical analysis of the odor to separate chemicals present in the sample odor. In some embodiments, the sensor array 110 may generate a chromatogram associated with the detected odor, which may include a spectrum of peaks representing one or more chemicals and/or analytes present in the detected odor.

The unmanned aerial vehicle 102 may perform sampling of odors in a particular area and/or adjacent areas for assessment. For example, the movement mechanisms 106 may provide movement to the unmanned aerial vehicle 102 to sample odor in multiple areas (e.g., two adjacent rooms). In some embodiments, the sensor array 110 may estimate an amount of odor (e.g., an odor concentration level) within the particular location. For example, the sensor array 110 may estimate an intensity of the odor which may be indicative of the amount of odor present. In some embodiments, the output from the sensory array 110 may be used as input to a pattern recognition unit 114, as will be described in further detail below.

In an embodiment, the sensor array 110 may estimate scent characteristics and/or scent gradients through time and space. For example, the unmanned aerial vehicle 102 may perform sampling of odors in a designated area over a period of time (e.g., minutes, days, weeks, etc.). In some embodiments, the unmanned aerial vehicle 102 may perform sampling of odors between a plurality of designated areas, such as adjacent rooms. The sensor array 110 may output a list of detected scents associated with a time of day, day of month, month of year, etc. that each scent was detected, a concentration level of each scent over a period of time, and/or location information, such a geographical coordinates, where each scent was detected. Accordingly, the sensor array 110 may provide a scent gradient for each detected scent associated with a particular location. In an embodiment, the scent gradient may include varying chemical compounds throughout a period of time. For example, the scent gradient may include multiple scents detected and/or multiple concentration levels of a particular scent. In some embodiments, the scent gradient may include varying concentration levels throughout a period of time.

In a further embodiment, the sensor array 110 may be configured to detect proximity to objects and/or obstacles in the path of the unmanned aerial vehicle 102 for any purpose such as, but not limited to, navigation guidance to the unmanned aerial vehicle 102. The sensor array 110 may be configured to determine a distance between the unmanned aerial vehicle 102 and a detected object.

The unmanned aerial vehicle 102 may include one or more collections units 112. In an embodiment, the collection units 112 may include a suction device (e.g., vacuum) and/or specialized compartments to collect an odor sample and/or to maintain that the odor sample comes into contact with odorless materials. For example, the collection units 112 may include a motorized door that may open while the unmanned aerial vehicle 102 is positioned and/or traveling through a particular area. In some embodiments, the suction device may draw ambient air having an odor (e.g., odor sample) into the collection unit 112. In an embodiment, the sensor array 110 may be positioned within the collection unit 112 such that the sensor array 110 may detect and/or identify the chemical compounds present in the odor sample.

The unmanned aerial vehicle 102 may include a pattern recognition unit 114 to identify the detected scent. In an embodiment, the pattern recognition unit 114 may receive scent information associated with the detected odor, such as a list of chemical compounds and/or chemical structure of the odor, from the sensor array 110. In a further embodiment, the pattern recognition unit 114 may include or otherwise be coupled to a database, the database storing a plurality of scents with corresponding chemical compounds and/or chemical structures associated with each scent (hereafter "identification information"). The pattern recognition unit 114 may compare the identification information with the information (e.g., list of chemical compounds, chemical structure, etc.) obtained from the sensor array 110 to identify the detected odor. Accordingly, the pattern recognition unit 114 may identify the detected odor. Recognition of detected scents may be performed for identification, comparison, quantification, and other applications, such as data storage and retrieval.

In some embodiments, the pattern recognition unit 114 may be updated to include identification information for a detected scent based on user input. For example, a user may input identification information for a detected scent via a secondary transmitter/receiver 130, such as a user device 132. The user device 132 may include, but is not limited to, a mobile device, tablet, computing device, etc. In an embodiment, the user may, via user device 132, input identification information which may be transmitted to the unmanned aerial vehicle 102 via transmission medium 126. For example, the user may identify the detected odor, if known. The unmanned aerial vehicle 102 may receive such identification information via transceiver 122 and may update the pattern recognition unit 114. Accordingly, the pattern recognition unit 114 may be trained for detecting odors associated with different varieties of scents.

In an embodiment, the unmanned aerial vehicle 102 may include a mapping unit 116. The mapping unit 116 may be configured to receive information from the sensor array 110 and/or pattern recognition unit 114 relating to the detected scent. The mapping unit 116 may perform an evaluation of characteristics associated with the detected odor to determine and/or estimate an assessment value. The assessment value may be based on, for example, the chemical substances, chemical structures, concentration levels, etc. of the detected odor. In some embodiments, the assessment value may be indicative of a pleasantness and/or unpleasantness of the detected odor. It should be noted that perception of an odor may change from pleasant to unpleasant depending on various factors, such as increasing concentration, intensity, time, frequency, and previous experience with a specific odor. For example, perception of an odor may change over a period of time, even if the chemical concentrations of the odor remain the same. The assessment value may be indicative of pleasantness dependent on these various factors. In an embodiment, the assessment value may be indicative of a safety level of the detected odor, especially when the detected odors include harmful substances.

In an embodiment, the mapping unit 116 may be configured to assess and/or map a hedonic tone (e.g., pleasantness and/or unpleasantness) associated with the detected scent on a predetermined hedonic scale. Such assessment may be indicative how pleasant a user will consider the detected odor. For example, the predetermined threshold value may be a level of unpleasantness tolerated by the user for the detected odor and/or may be a level of pleasantness tolerated by the user. In an embodiment, the predetermined threshold value may be a minimum value associated with a particular scent, such as a minimum concentration level. In some embodiments, the mapping unit 116 may be configured to estimate a safety level of the detected odor.

In some embodiments, the mapping unit 116 may include an olfactometer or similarly functioning device to detect and/or measure odor dilution. The mapping unit 116 may employ hedonic assessment to scale the detected odors on a scale ranging from unpleasant to neutral to pleasant. For example, the mapping unit 116 may scale the detected odor on a perceptual axis of odorant pleasantness, such as an axis ranging from very unpleasant to very pleasant. In an embodiment, the mapping unit 116 may scale the detected odors on a scale ranging from safe to unsafe. The assessment value estimated by the mapping unit 116 may be indicative of pleasantness and/or safeness of a detected scent.

In some embodiments, the hedonic tone of a detected odor may be based on several factors, including concentration levels of the detected scent, intensity of the detected scent, time of day, frequency of the detected scent (e.g., how often the scent is present), user input, level of perception based on recipient, etc. For example, certain properties of an odor may appear to have different hedonic tone in the morning or evening, based on the weather, status of the air (e.g., humidity), sunshine, and/or personal sensitiveness which may vary during the day. Generally, the term concentration refers to an amount of a substance or to a number of molecules. Odor perception often depends on the concentration (e.g., number of molecules) available to olfactory receptors. The term intensity generally is a perceived strength of odor sensation. Sometimes the perceived strength of an odor sensation is measured in conjunction with odor concentration. In an embodiment, the intensity (e.g., perceived strength) may be modeled by the Weber-Fechner law as follows: $I=A \times \log(C)+B$, where I is the perceived psychological intensity at the dilution step on a butanol scale, A is the Weber-Fechner coefficient, C is the chemical concentration level, and B is a constant.

In some embodiments, the mapping unit 116 may scale the hedonic tone associated with the detected scent based on known sensitivities to odors, especially when the detected scent is confined in indoor environments. For example, a user may define personal sensitivities to certain odors which may be stored in the pattern recognition unit 114. In some embodiments, the pattern recognition unit 114 may include a preliminary level of pleasantness/unpleasantness for each known odor. The preliminary level may be periodically and/or intermittingly updated to reflect sensitivities of the user such that the level of pleasantness/unpleasantness is learned for different users. In an embodiment, the sensor array 110 (e.g., proximity detector) may determine whether or not the unmanned aerial vehicle 102 is in an indoor or outdoor environment, such as detecting surrounding objects (e.g., walls, trees, etc.).

In an embodiment, the mapping unit 116 may be configured to perform hedonic assessment by taking into account one or more variables. The one or more variables may include gradients of odors through time and space, wind characteristics, air conditioning, ability of a recipient to smell the odor, etc. For example, each scent may be annotated in the mapping unit 116 and/or pattern recognition unit 114 with multiple tags, such as time, space, context, etc. In some embodiments, different weights may be associated with different attributes based on a user's or a group's characteristics. In some embodiments, the mapping unit 116 performs hedonic assessment in combination with one or more components on the unmanned aerial vehicle 102. The mapping unit 116 may perform hedonic assessment in conjunction with a camera, such as camera 118, which will be described in further detail below.

In some embodiments, the mapping unit 116 may generate an instruction to one or more components of the unmanned aerial vehicle 102 to perform at least one function when the assessment value exceeds a predetermined threshold value. The predetermined threshold value may be stored in a database, such as the pattern recognition unit 114, and/or may be input by a user via user input device 132. Accordingly, a user may be able to train the pattern recognition unit 114 and/or mapping unit 116 based on sensitivities of the particular user. For example, the user may set the threshold value to a level of unpleasantness perceived by the user for each detected scent.

The at least one function may include activating one or more feedback output components on the unmanned aerial vehicle 102. For example, the at least one function may include dispersing at least one scent, such as, but not limited to, a pleasant scent, air freshener and/or odor neutralizing product, via a scent release mechanism 120, such as when the detected odor is very unpleasant.

Assume the sensor array 110 detects a desirable presence of 2-acetyl-1-pyrroline (2AP) in a particular location. Over a period of time, however, the concentration level of the 2AP may decrease. Accordingly, the mapping unit 116 may estimate an assessment value, including concentration of the 2AP, and may activate one or more feedback output components to perform a function, such as dispersing a scent. The unmanned aerial vehicle 102 may disperse more 2AP to increase the presence of 2AP in the particular location. In an embodiment, the unmanned aerial vehicle 102 may detect/determine that 2AP has been present in the particular area for a period of time (e.g., the past 4 hours), and individuals may become accustomed to the 2AP scent. Thus, the perception of 2AP may be decreasing or it may even grow bothersome to some individuals. Accordingly, the mapping unit 116 may disperse an alternative scent. For example, after 3 hours, the unmanned aerial vehicle 102 may disperse other compounds, such as 2,3-butanedione (more commonly known as diacetyl) and/or methional.

In an embodiment, the at least one function may include, for example, transmitting an alert to a secondary transmitter/receiver 130, via a transceiver 122, such as when the detected odor includes particularly harmful substances/chemicals. For example, the alert may be sent to a monitoring system 136 used by security personnel indicating that the detected odor includes a harmful substance and/or emergency services may be needed.

In an embodiment, the unmanned aerial vehicle 102 may include a camera 118. The camera 118 may be configured to provide visual feedback to the unmanned aerial vehicle 102, including one or more still images and/or video feedback. The camera 118 may be employed with, for example, the mapping unit 116 to estimate the assessment value. In some embodiments, the camera 118 may be configured to detect one or more individuals (e.g., humans). For example, the camera 118 may capture still images and/or video feedback including one or more individuals, detect the one or more individuals, and/or monitor emotions of the one or more individuals. The camera 118 may capture one or more still images or video images and, using a database, may perform image comparison with database images to detect and/or monitor the individuals.

In an embodiment, the camera 118 may be configured to detect an elderly individual. Generally, elderly individuals may have less olfactory sensitivity. The camera 118 may detect one or more elderly individuals using image comparison, and provide such information to the mapping unit 116. In an embodiment, the mapping unit 116 may perform hedonic assessment of a detected scent based on the characteristics of the recipients, especially since elderly recipients may have a reduced ability to smell an odor. For example, the mapping unit 116 may estimate an assessment value having a decreased value, such as a detected scent with low concentration levels being less unpleasant, since an elderly individual may be unable to smell the detected scent.

In an embodiment, the camera 118 may be configured to detect emotions of one or more individuals. For example, the camera 118 may capture one or more still images or video including emotions of one or more individuals (e.g., happy emotions, sad emotions, etc.) and, using a database, may perform image comparison with database images to identify emotions of the individuals. Emotions may be detected by, for example, visually assessing facial expressions of the individuals to determine mood of an individual. In some embodiments, the unmanned aerial vehicle 102 may disperse one or more scents directed toward the individuals when certain emotions are identified. Certain scents may help individuals in certain situations, such as altering an individual's mood, cognitive, psychological and/or physical well-being. For example, lavender scents are known to help individuals sleep. Vanilla scents can elevate an individual's mood. The unmanned aerial vehicle 102 may disperse one or more scents upon detection of at least one emotion to, for example, alleviate stress, energize, sharpen and/or boost concentration, ease depression, suppress appetite, reduce pain and/or anxiety, relaxation, etc.

In some embodiments, the camera 118 may employ computer-vision algorithms to identify a source of a detected odor. For example, when an odor is detected, the camera 118 may capture still images and/or video of objects within the vicinity of the detected odor. The camera 118 may, using image comparison and/or a database, identify a source of a detected odor. For example, assume the sensor array 110 detects an odor of an orange. The camera 118 may capture still images and/or video within the vicinity of the detected odor and, using computer-vision algorithms, the camera 118 may identify the source of the odor. (e.g., oranges on a table).

In an embodiment, the camera 118 may capture still images and/or video of a particular object and determine and/or estimate the state of the particular object. For example, the camera 118 may identify produce (e.g., fruits or vegetables) and estimate the state of the produce, such as freshness of the fruits or vegetables. Freshness of produce may be determined by, for example, bruising, color, mold, etc. In an embodiment, the camera 118 may identify whether a product is broken or otherwise impaired in some way, such as having an opened seal on a bag, can, etc. of the product, or a broken box containing the product. In some embodiments, the unmanned aerial vehicle 102 may disperse one or more scents directed toward the particular object to reflect the state (e.g., freshness) of the product. Dispersing a scent to resemble the freshness of a product may be employed for marketing the particular product, improving enjoyment of shoppers and or people with allergies, and/or marking unpleasant smells.

In a further embodiment, the camera 118 may be configured to provide visual feedback of obstacles in the path of the unmanned aerial vehicle 102 for any purpose, such as, but not limited to, navigation guidance to the unmanned aerial vehicle 102. It should be understood that various types of cameras are contemplated, including night-vision enabled cameras, infrared sensing cameras, high-definition cameras, X-ray imaging devices, line scan imaging devices, etc.

In some embodiments, the camera 118 may be placed on the unmanned aerial vehicle 102 such that the camera 118 may provide visual feedback in 360 degrees on a horizontal plane and/or 360 degrees on a vertical plane of the unmanned aerial vehicle 102. In some embodiments, the camera 118 may include a plurality of cameras to provide visual feedback in all directions surrounding the unmanned aerial vehicle 102 such that there are no obscurations of the visual field (e.g., blind spots). In further embodiments, the camera 118 may be embedded within the housing unit 104 so as to prevent any negative effects to the aerodynamics of the unmanned aerial vehicle 102.

The unmanned aerial vehicle 102 may include one or more scent release mechanisms 120. The scent release mechanism 120 may include a spray nozzle, compartment, reservoir, and/or similarly functioning devices that facilitate containment and/or dispersion of a gaseous substance (e.g., scent). In some embodiments, the scent release mechanism 120 may include a reservoir storing a liquid and/or solid aromatic substance, the reservoir being coupled to an opening and/or nozzle for disbursing one or more scents to a particular location. The scent release mechanism 120 may include a pressurization unit (not shown) to release the aromatic substance under pressure. In some embodiments, the scent release mechanism 120 may control an intensity and/or amount of the aromatic substance released. For example, the scent release mechanism 120 may release a controlled amount of aromatic substance using one or more valves controlled by the mapping unit 116. In an embodiment, the scent release mechanism 120 may release a controlled value for the intensity and/or concentration level of the aromatic substance. The one or more scent release mechanisms 120 may be externally located on the unmanned aerial vehicle 102 and/or internally within the unmanned aerial vehicle 102.

In an embodiment, the scent release mechanism 120 may include a light-emitting diode (LED), a heat generator, and/or heat absorption device. In an embodiment, the components of the scent release mechanism may be controlled by the mapping unit 116. The scent release mechanism 120 may, in some embodiments, heat the liquid and/or solid aromatic substance for dispersion. Lighting the path for the scent release can be done by the LED. Heating the scent may, at least partly, encourage volatilization, vaporization, and/or dispersion of a liquid in a compartment on the unmanned aerial vehicle 102, thereby causing a phase transition from the liquid phase to vapor in an effort to more effectively spread the vaporized scent particles. In some embodiments, heating the scent may be beneficial for therapeutic purposes, but also in settings like hunting where scents (e.g., pheromones) can be used to attract potential game. The release of one or more scents may be used to alleviate stress, energize, sharpen and/or boost concentration, ease depression, suppress appetite, reduce pain and/or anxiety, relaxation, etc. In addition, the release of one or more scents may be used to market and/or advertise certain products. For example, a scent associated with a product may be dispersed to further market that product. The scent release mechanism 120 may release one or more scents in any setting and/or environment, such as in hospitals, casinos, hotels, automobiles, treatment plants, etc.

The scent release mechanism 120 may disperse a pleasant scent, air freshener, chemical neutralizing agent, odor neutralizing product, etc. when the assessment value exceeds a predetermined threshold value. For example, the scent release mechanism 120 may disperse an odor neutralizing agent when an unpleasant scent is detected, the unpleasant scent exceeding the predetermined threshold value. In some embodiments, the scent release mechanism 120 may disperse a chemical neutralizing agent to neutralize and/or remove unsafe chemical substances from the air when the assessment value exceeds a predetermined threshold value, such as when unsafe chemical substances in the odor sample are detected.

In an embodiment, the movement mechanisms 106 may provide aerial movement to the unmanned aerial vehicle 102 to the particular location where the identified odor was detected. In addition, the movement mechanisms 106 may provide aerial movement to the unmanned aerial vehicle 102 such that scent dispersal via the scent release mechanism 120 is directed towards the particular location and/or enables the unmanned aerial vehicle 102 to disperse one or more scents throughout the particular location.

The unmanned aerial vehicle 102 may include a propulsion device 124. The propulsion device 124 may include, but is not limited to, one or more propulsive nozzles, bladeless fans, fans, air multipliers, etc. In some embodiments, the propulsion device 124 may generate airflow directed towards the detected scent. The airflow may dissipate the detected odor and/or "push" the detected odor away from a particular area. In some embodiments, the camera 118 and/or sensor array 110 may detect one or more ventilation points in a particular area and the propulsion device 124 may generate airflow directed towards the one or more ventilation points to push the detected scent toward the ventilation points. For example, the camera 118 may use image comparison to detect the ventilation points. In an embodiment, the sensor array 110 may estimate airflow in a particular area (e.g., a room) to detect the ventilation points. In some embodiments, the propulsion device 124 may be activated when the assessment value exceeds the predetermined threshold value.

In an embodiment, the unmanned aerial vehicle 102 may include a transceiver 122 or similarly functioning device(s). The transceiver 122 may be configured to communicate via transmission medium 126 with one or more secondary transmitter/receiver devices 130, such as a user device 132 (e.g., a mobile device, tablet, computing device, etc.), one or more unmanned aerial vehicles 134 (e.g., secondary drones), and/or a monitoring system 136. For example, the monitoring system 136 may include a computing device used by emergency services (e.g., an alarm system).

The transceiver 122, which may include a wireless module, may communicate with the wireless modules of other devices, allowing for the formation of a mesh network. The wireless module may include a low-power wireless transmitter, for example using a wireless protocol such as WirelessHART®, ZigBee®, Bluetooth®, 6LoWPAN, or Wi-Fi®, that connects to the wireless modules of additional devices. A mesh network is a multi-hop network wherein each unmanned aerial vehicle 102 and/or secondary devices 130 can be both a source and a relay communication node.

In some embodiments, the transceiver 122 may communicate with each of the secondary devices 130 to relay detected odor information and/or instructions to perform one or more functions when the assessment value exceeds the predetermined threshold. For example, the transceiver 122 may communicate with one or more secondary drones 134 to provide scent distribution in an odor gradient. The unmanned aerial vehicle 102 and/or secondary drones 134 may be arranged in a sequential order such that the first unmanned aerial vehicle 102 distributes a minimum value of a particular scent and each subsequent secondary drone 134 distributes an increasing amount of the particular scent until a maximum value is achieved. In an embodiment, the unmanned aerial vehicle 102 and/or secondary drones 134 may be arranged in a sequential order such that the first unmanned aerial vehicle 102 distributes a particular value of a particular scent and each subsequent secondary drone 134 distributes various amounts of the particular scent until a pattern of scents is distributed through a space. In order to maintain the pattern or gradient of scents, the drones may move through time as useful to generate, maintain, and/or approximate a scent pattern. In an embodiment, the transceiver 122 may communicate with a monitoring system 136, such as those used by emergency personnel, to indicate a harmful substance is detected and/or that emergencies services may be needed.

It is to be appreciated that system 200 described below with respect to FIG. 2, and system 300 described below with respect to FIG. 3, are systems for implementing respective embodiments of the present principles. Part or all of processing system 100 may be implemented in one or more of the elements of system 200 of FIG. 2 and/or system 300 of FIG. 3. Further, it is to be appreciated that processing system 100, 200 and/or 300 may perform at least part of the method described herein, including, for example, at least part of method 400 of FIG. 4.

Figure 2:
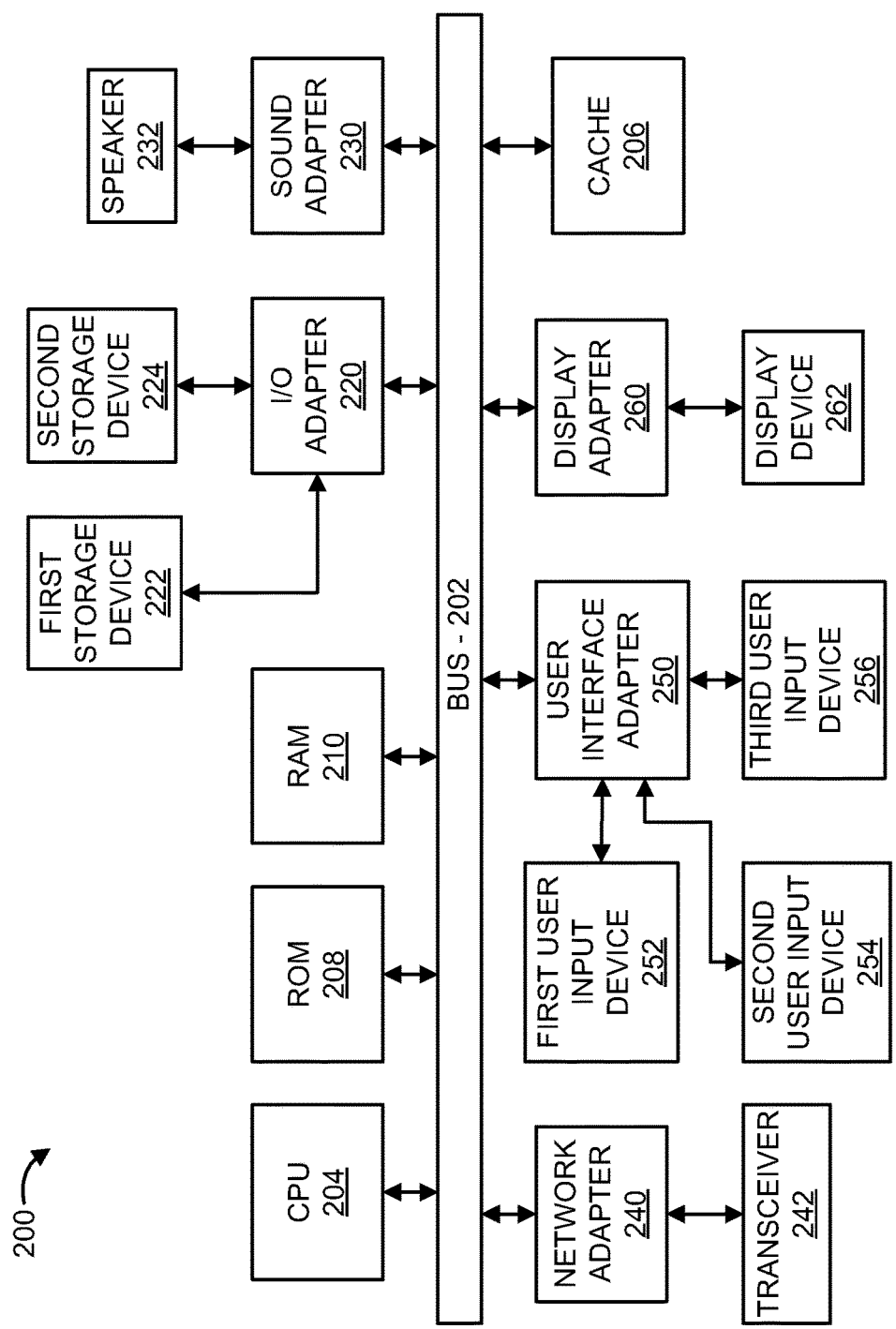
FIG. 2 is a block/flow diagram of an exemplary processing system for scent analysis using an unmanned aerial vehicle, in accordance with an embodiment of the present principles.

Now referring to FIG. 2, with continued reference to FIG. 1, an exemplary processing system 200 to which the present principles may be applied, in accordance with an embodiment, is illustratively depicted. The processing system 200 includes at least one processor, such as a computer processing unit (CPU) 204, operatively coupled to other components via a system bus 202. A cache 206, a Read Only Memory (ROM) 208, a Random Access Memory (RAM) 210, an input/output (I/O) adapter 220, a sound adapter 230, a network adapter 240, a user interface adapter 250, and a display adapter 260 are operatively coupled to the system bus 202.

A first storage device 222 and a second storage device 224 are operatively coupled to system bus 202 by the I/O adapter 220. The storage devices 222 and 224 can be any of a disk storage device (e.g., a magnetic or optical disk storage device), a solid state magnetic device, etc. The storage devices 222 and 224 can be the same type of storage device or different types of storage devices. In one embodiment, database images of detected images may be stored on the first storage device 222 and/or the second storage device 224 for comparison with images obtained by the camera 110 of FIG. 1.

A speaker 232 is operatively coupled to system bus 202 by the sound adapter 230. In one embodiment, the unmanned aerial vehicle 102 may be configured to generate a command, instruction, or audio signal, such as a beep and/or beat, from the speaker 232. For example, the unmanned aerial vehicle 102 may generate a warning signal (e.g., an alarm) when harmful substances in a detected odor are identified such that individuals are aware of the presence of such substances. This may be especially important in situations where scents are odorless but still include harmful substances and/or chemicals, such as carbon monoxide.

A transceiver 242 is operatively coupled to system bus 202 by network adapter 240. A display device 262 is operatively coupled to system bus 202 by display adapter 260. In an embodiment, the display device 262 may be configured to display alerts visible to individuals, such as a warning of chemical substances detected in a particular area.

A first user input device 252, a second user input device 254, and a third user input device 256 are operatively coupled to system bus 202 by user interface adapter 250. The user input devices 252, 254, and 256 can be any type of input device, including but not limited to, a keyboard, a mouse, a keypad, an image capture device, a motion sensing device, a microphone, a device incorporating the functionality of at least two of the preceding devices, and so forth. Other types of input devices can also be used while maintaining the spirit of the present principles. The user input devices 252, 254, and 256 can be the same type of user input device or different types of user input devices. The user input devices 252, 254, and 256 are used to input and output information to and from system 200. For example, the user input devices 252, 254, and 256 may be employed to identify detected scents and/or provide user sensitivities to the unmanned aerial vehicle 102.

The processing system 200 may also include other elements (not shown) or may omit some elements as shown. For example, various other input devices and/or output devices can be included in processing system 200 depending upon the particular implementation of the same, such as various types of wireless and/or wired input and/or output devices. Moreover, additional processors, controllers, memories and so forth, in various configurations, can also be utilized. These and other variations of the processing system 200 are readily contemplated.

Referring now to FIG. 3, with continued reference to FIG. 1, an exemplary system 300 for scent analysis using an unmanned aerial vehicle 102 is illustratively depicted, in accordance with an embodiment of the present principles. The system 300 includes a steering controller 302, a navigation unit 304, a sensing device 306, a database 308, a mapping unit 310, and/or a scent release mechanism 312.

The steering controller 302 may be configured to control movement of the unmanned aerial vehicle 102. In one embodiment, the steering controller 302 may include a motor, such as motor 108 in FIG. 1. In some embodiments, the steering controller 302 may control the aerial movement of the unmanned aerial vehicle 102 by controlling the at least one movement mechanism 106 and/or motor 108 illustrated in FIG. 1.

In an embodiment, the steering controller 302 may be configured to control movement of the unmanned aerial vehicle 102 by controlling the rotational speed(s) and/or rotational direction(s) of each of the movement mechanisms 106 independently. For example, the steering controller 302 may be configured to rotate each of the movement mechanisms 106 in a single direction, or alternatively, the steering controller 302 may be configured to rotate each of the movement mechanisms 106 in opposing directions. In one embodiment, the steering controller 302 may be configured to control movement of the unmanned aerial vehicle 102 to move the unmanned aerial vehicle 102 to particular locations, such as towards one or more detected scents and/or odors, and/or around/over difficult terrain and/or obstacles (e.g., walls, doorways, etc.).

In a further embodiment, the system 300 may include a navigation unit 304, such as a global positioning system (GPS). The navigation unit 304 may provide location information to the steering controller 302. For example, the navigation unit 304 may include map coordinates of a particular area, such as a floor plan of a building, and may provide such information to the steering controller 302, such that the steering controller 302 may direct the unmanned aerial vehicle 102 to a particular location. In an embodiment, the navigation unit 304 may provide geolocation coordinates of one or more detected scents to identify the particular area where a scent is detected. Accordingly, each scent may be associated with a particular location.

In an embodiment, the system 300 may include a sensing device 306. The sensing device 306 may include a camera, a sensor, a radar system or similarly functioning devices. In an embodiment, the sensing device 306 may include a plurality of sensors, such as a sensor array 110 as illustrated in FIG. 1. The sensing device 306 may detect chemical stimuli and/or chemical substances in an environment. In an embodiment, the sensing device 306 may be configured to sample ambient air in a particular location and detect one or more scents and/or chemicals within the particular location. The sensing device 306 may perform chemical analysis of ambient air to generate a chromatograph (e.g., a separation of chemicals present in the ambient air). In an embodiment, the sensing device 306 may estimate scent characteristics and/or scent gradients through time and space.

The system 300 may include a database 308, such as a pattern recognition unit 114 of FIG. 1. The database 308 may receive, as input, information associated with a detected scent from the sensing device 306. For example, the database 308 may receive scent information associated with the detected odor, such as a list of chemical compounds and/or chemical structure of the odor, from the sensing device 306. The database 308 may include a list of a plurality of scents with corresponding chemical compounds and/or chemical structures associated with each scent. In an embodiment, the database 308 may compare the scent information (e.g., list of chemical compounds, chemical structure, etc.) from the sensing device 306 with identification information stored in the database 308 to identify the detected odor. In some embodiments, user's sensitivities to certain odors, concentration levels, and/or intensity levels may be stored in the database 308. Accordingly, the database 308 may identify the detected odor.

In an embodiment, the database 308 may include still images or video including emotions of one or more individuals (e.g., happy emotions, sad emotions, etc.) and may perform image comparison to identify emotions of one or more individuals in a particular location. The database 308 may include still images or video of one or more objects and may perform image comparison to identify a source of a detected odor.

In some embodiments, the database 308 may be updated to include identification information for a detected scent. For example, a user may input identification information for a detected scent, and the database 308 may update the information associated with the detected scent. Accordingly, the database 308 may be trained for detecting odors associated with different varieties of scents.

The system 300 may include a mapping unit 310 to determine and/or estimate an assessment value associated with a detected odor. The assessment value may be based on, for example, the chemical substances, chemical structures, concentration levels, etc. of the detected odor, etc., and/or user sensitivities to the detected odor. In some embodiments, the assessment value may be indicative of a pleasantness and/or unpleasantness of the detected odor. For example, the mapping unit 310 may assess and/or map a hedonic tone (e.g., pleasantness and/or unpleasantness) associated with the detected scent on a predetermined hedonic scale. The hedonic tone of a detected odor may be based on several factors, including concentration levels of the detected scent, intensity of the detected scent, time of day the scent is detected, frequency of the detected scent, user input, etc. In an embodiment, the assessment value may be indicative of a safety level of the detected odor, especially when the detected odors include harmful substances.

In some embodiments, the mapping unit 310 may generate an instruction to and/or control one or more components of the unmanned aerial vehicle 102 to perform at least one function when the assessment value exceeds a predetermined threshold value. The at least one function may include, for example, dispersing a pleasant scent, air freshener and/or odor neutralizing product, via a scent release mechanism 312, such as when the detected odor is very unpleasant. The scent release mechanism 312 may include a spray nozzle, compartment, reservoir, and/or similarly functioning devices that facilitate containment and/or dispersion of a gaseous substance. In some embodiments, the scent release mechanism 312 may control an intensity and/or amount of an aromatic substance released. For example, the scent release mechanism 312 may release a controlled amount of aromatic substance. In some embodiments, the scent release mechanism 312 may adjust the amount of aromatic substance released dependent on the detected odor, such as concentration level and/or level of unpleasantness of the detected odor.

The scent release mechanism 312 may disperse a pleasant scent, air freshener, chemical neutralizing agent, odor neutralizing product, etc. when the assessment value exceeds a predetermined threshold value. In an embodiment, the release of one or more scents may be used to alleviate stress, energize, sharpen and/or boost concentration, ease depression, suppress appetite, reduce pain and/or anxiety, relaxation, etc. In addition, the release of one or more scents may be used to market and/or advertise certain products.

In the embodiment shown in FIG. 3, the elements thereof may be interconnected by a bus 301. However, in other embodiments, other types of connections can also be used. Moreover, in an embodiment, at least one of the elements of system 300 is processor-based. Further, while one or more elements may be shown as separate elements, in other embodiments these elements can be combined as one element. These and other variations of the elements of system 300 are readily determined by one of ordinary skill in the art, given the teachings of the present principles provided herein.

Figure 4:
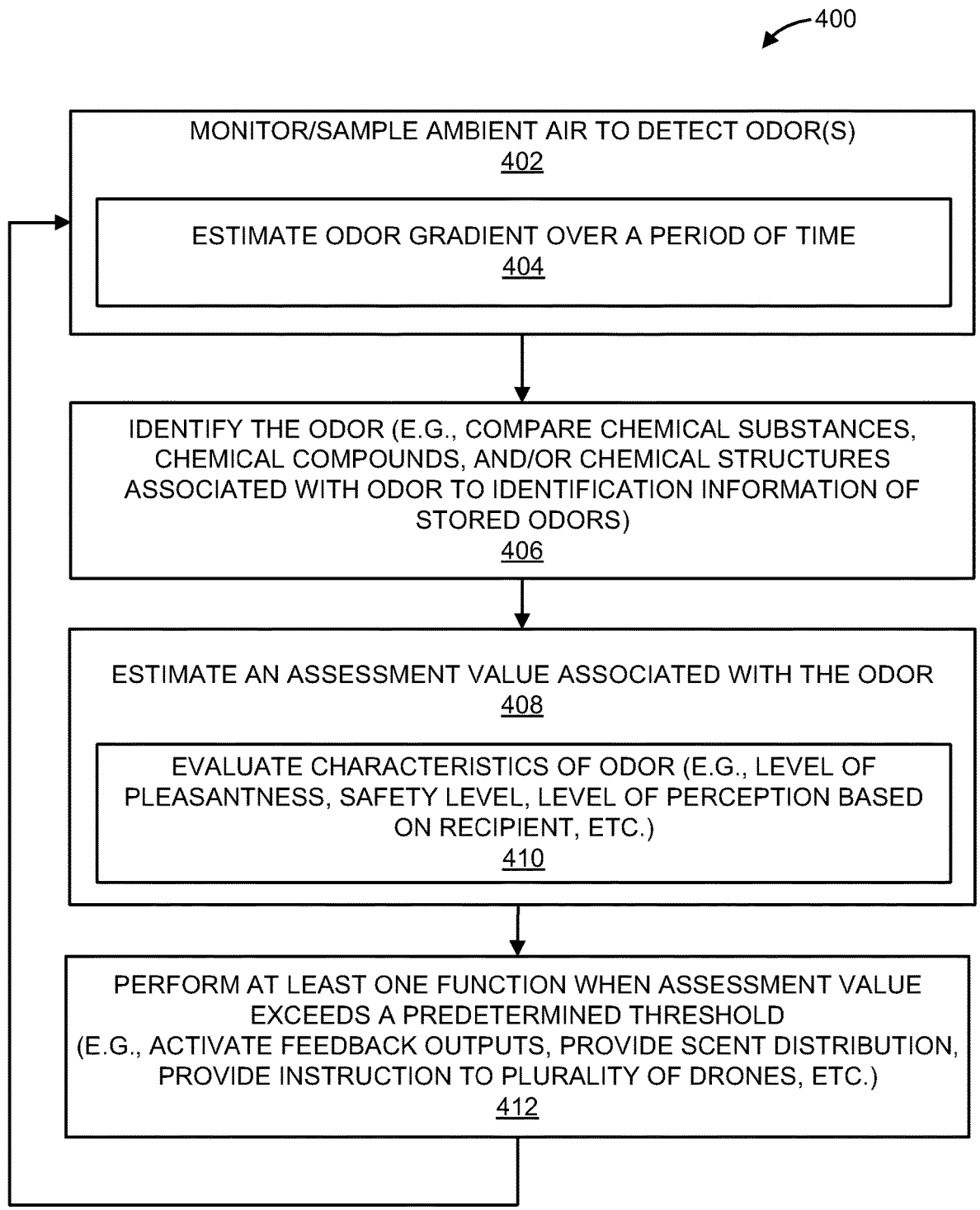
FIG. 4 is a block/flow diagram of an exemplary method for scent analysis using an unmanned aerial vehicle, in accordance with an embodiment of the present principles.

Now referring to FIG. 4, with continued reference to FIGS. 1-3, FIG. 4 shows an exemplary method 400 for scent analysis using an unmanned aerial vehicle 102, in accordance with an embodiment of the present principles.

In block 402, the method 400 may include monitoring and/or sampling ambient air in at least one location to detect at least one odor. The odor may be associated with one or more chemical substances, chemical compounds, or chemical structures. In some embodiments, the monitoring and/or sampling may be performed by a processor-based monitoring device, such as sensor array 110 of FIG. 1 and/or sensing device 306 of FIG. 3. In an embodiment, monitoring ambient air may include estimating an odor gradient, such as varying concentration levels of a detected odor, over a period of time and/or in a plurality of different locations (e.g., adjacent rooms), as shown in block 404.

In block 406, the method 400 may include identifying the detected odor. For example, a database may be used in conjunction with a processing device to compare the detected odor(s) to identification information stored in the database. The detected odor(s) may be associated with and/or include chemical substances, chemical compounds, chemical structures, etc. that may be employed to identify the detected odor. The identification information may be updated to include user set values, such as odors identified by the user, and/or user sensitivities (e.g., level of pleasantness tolerated by the user).

In block 408, the method 400 may include estimating an assessment value associated with the detected odor. The assessment value may be based on one or more variables, such as concentration level of the odor, detection time of the odor, frequency of detection of the odor, and/or user input. In some embodiments, the assessment value may be indicative of a level of pleasantness of the odor, as illustrated in block 410. In an embodiment, the assessment value may be indicative of a safety level of the odor. In a further embodiment, estimating the assessment value may include evaluating one or more characteristics associated with at least one individual (e.g., emotions, age, etc.), and estimating the assessment value based on the one or more characteristics of the individual(s). Accordingly, the method 400 may include estimating the assessment value based on level of perception of a recipient to perceive the odor.

In block 412, the method 400 may include automatically performing at least one function when the assessment value exceeds a predetermined threshold value. For example, the predetermined threshold value is a level of unpleasantness tolerated by the user for odor or a safety level of an odor, such as a concentration level safe for inhalation purposes. The at least one function includes activating one or more feedback outputs on the unmanned aerial vehicle 102. For example, the at least one function may include distributing at least one scent, such as a pleasant scent, air freshener and/or an odor neutralizing product. In an embodiment, the at least one function may include controlling a concentration level of the at least one scent distributed.

The at least one function may include providing an instruction to a plurality of drones 134 to distribute a scent gradient of the scent to be distributed. For example, a first drone may distribute and/or disperse a minimum value of the scent and each subsequent drone may distribute an increased amount of the scent until a maximum value of the scent is distributed. It should be understood that the blocks of 402-412 may be continuously repeated or may discontinue when an odor is no longer detected.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 5:
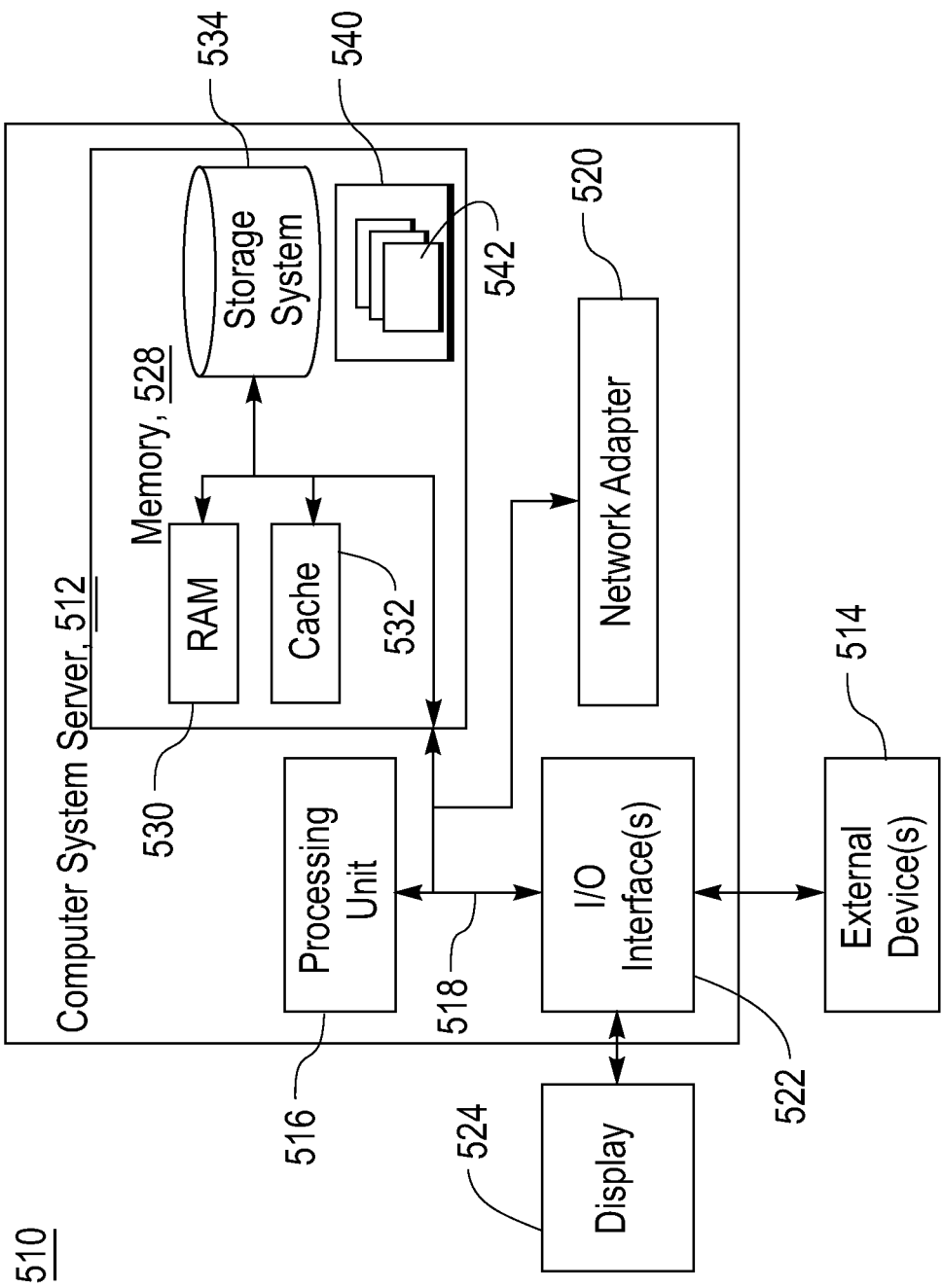
FIG. 5 is a block/flow diagram of an exemplary cloud computing node, in accordance with an embodiment of the present principles.

Referring now to FIG. 5, a schematic of an example of a cloud computing node 510 is shown. Cloud computing node 510 is only one example of a suitable cloud computing node and is not intended to suggest any limitation as to the scope of use or functionality of embodiments of the invention described herein. Regardless, cloud computing node 510 is capable of being implemented and/or performing any of the functionality set forth hereinabove.

In cloud computing node 510 there is a computer system/server 512, which is operational with numerous other general purpose or special purpose computing system environments or configurations. Examples of well-known computing systems, environments, and/or configurations that may be suitable for use with computer system/server 512 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 512 may be described in the general context of computer system executable instructions, such as program modules, being executed by a computer system. Generally, program modules may include routines, programs, objects, components, logic, data structures, and so on that perform particular tasks or implement particular abstract data types. Computer system/server 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 512 in cloud computing node 510 is shown in the form of a general-purpose computing device. The components of computer system/server 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 512 typically includes a variety of computer system readable media. Such media may be any available media that is accessible by computer system/server 512, and it includes both volatile and non-volatile media, removable and non-removable media.

System memory 528 can include computer system readable media in the form of volatile memory, such as random access memory (RAM) 530 and/or cache memory 532. Computer system/server 512 may further include other removable/non-removable, volatile/non-volatile computer system storage media. By way of example only, storage system 534 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system/server 512 may also communicate with one or more external devices 614 such as a keyboard, a pointing device, a display 524, etc.; one or more devices that enable a user to interact with computer system/server 512; and/or any devices (e.g., network card, modem, etc.) that enable computer system/server 512 to communicate with one or more other computing devices. Such communication can occur via Input/Output (I/O) interfaces 522. Still yet, computer system/server 512 can communicate with one or more networks such as a local area network (LAN), a general wide area network (WAN), and/or a public network (e.g., the Internet) via network adapter 520. As depicted, network adapter 520 communicates with the other components of computer system/server 512 via bus 518. It should be understood that although not shown, other hardware and/or software components could be used in conjunction with computer system/server 512. Examples, include, but are not limited to: microcode, device drivers, redundant processing units, external disk drive arrays, RAID systems, tape drives, and data archival storage systems, etc.

Figure 6:
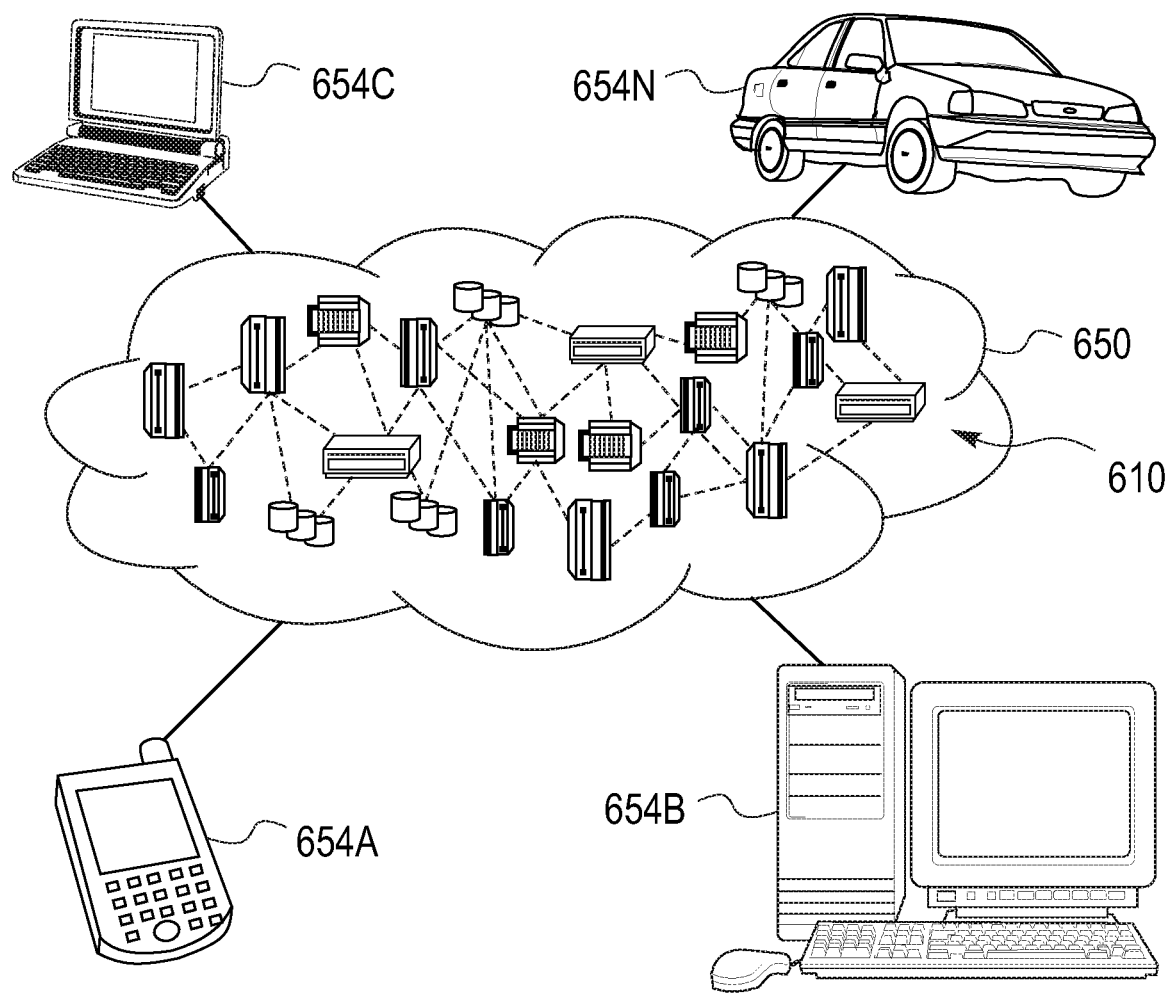
FIG. 6 is a block/flow diagram of an exemplary cloud computing environment, in accordance with an embodiment of the present principles.

Referring now to FIG. 6, illustrative cloud computing environment 650 is depicted. As shown, cloud computing environment 650 includes one or more cloud computing nodes 610 with which local computing devices used by cloud consumers, such as, for example, personal digital assistant (PDA) or cellular telephone 654A, desktop computer 654B, laptop computer 654C, and/or automobile computer system 654N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N shown in FIG. 6 are intended to be illustrative only and that computing nodes 610 and cloud computing environment 650 can communicate with any type of computerized device over any type of network and/or network addressable connection (e.g., using a web browser).

Referring now to FIG. 7, a set of functional abstraction layers provided by cloud computing environment 650 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 760 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 762 provides an abstraction layer from which the following examples of virtual entities may be provided: virtual servers; virtual storage; virtual networks, including virtual private networks; virtual applications and operating systems; and virtual clients.

In one example, management layer 764 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 766 provides examples of functionality for which the cloud computing environment may be utilized. Examples of workloads and functions which may be provided from this layer include: mapping and navigation; software development and lifecycle management; virtual classroom education delivery; data analytics processing; transaction processing; and scent analysis.

Having described preferred embodiments of an unmanned aerial vehicle for scent analysis and distribution, which are intended to be illustrative and not limiting, it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. An unmanned aerial vehicle for air sampling, the unmanned aerial vehicle comprising:

a sensor array including sensors configured to sample ambient air in at least one location to detect at least one odor;

a pattern recognition unit coupled to a database to identify the at least one odor, wherein the at least one odor is compared to identification information stored in the database, the pattern recognition unit being further configured to identify a source of the at least one odor using pattern recognition; and a mapping unit configured to estimate an assessment value associated with the at least one odor, the assessment value including a hedonic assessment scaling the at least one odor on a perceptual axis reflecting a level of odorant pleasantness; and configured to control distribution of at least one scent selected to impact the at least one odor when the assessment value exceeds a predetermined threshold on a hedonic scale.

2. The unmanned aerial vehicle of claim 1, further comprising a scent release mechanism to distribute, under the control of the mapping unit, at least one scent includes an odor neutralizing agent selected to neutralize the at least one odor.

3. The unmanned aerial vehicle of claim 2, wherein the scent release mechanism is configured to control a concentration level of the at least one scent distributed.

4. The unmanned aerial vehicle of claim 2, further comprising a transceiver to transmit an instruction to a plurality of drones to distribute a scent gradient of the at least one scent such that a first drone distributes a minimum value of the at least one scent and each subsequent drone distributes an increased amount of the at least one scent until a maximum value of the at least one scent is distributed.

5. The unmanned aerial vehicle of claim 1, wherein the sensor array includes a plurality of chemoreceptors to estimate an odor gradient associated with the at least one odor over a period of time.

6. The unmanned aerial vehicle of claim 1, wherein the assessment value of the at least one odor is based on one or more variables, the one or more variables being selected from the group consisting of concentration level of the at least one odor, detection time of the at least one odor, frequency of detection of the at least one odor, and user input.

7. The unmanned aerial vehicle of claim 1, wherein the identification information includes one or more sensitivities associated with a user.

8. The unmanned aerial vehicle of claim 7, wherein the assessment value is indicative of a level of pleasantness of the at least one odor and the predetermined threshold value is a level of unpleasantness tolerated by the user for the at least one odor.

9. The unmanned aerial vehicle of claim 1, wherein the assessment value is indicative of a safety level of the at least one odor.

10. The unmanned aerial vehicle of claim 1, wherein the sensor array includes a camera to identify a source of the at least one odor.

11. The unmanned aerial vehicle of claim 1, wherein the sensor array includes a camera to detect one or more characteristics associated with at least one individual, wherein the mapping unit is further configured to estimate the assessment value based on the one or more characteristics of the at least one individual.

12. The unmanned aerial vehicle of claim 11, wherein the one or more characteristics includes an emotion expressed by the at least one individual.

13. A method for air sampling using an unmanned aerial vehicle, the method comprising:
sampling ambient air in at least one location to detect at least one odor;
identifying, using a database, the at least one odor, wherein the at least one odor is compared to identification information stored in the database;
identifying a source of the at least one odor using pattern recognition;
estimating an assessment value associated with the at least one odor, the assessment value including a hedonic assessment scaling the at least one odor on a perceptual axis reflecting a level of odorant pleasantness; and
automatically distributing at least one scent selected to impact the at least one odor when the assessment value exceeds a predetermined threshold on a hedonic scale.

14. The method of claim 13, wherein distributing at least one scent includes distributing an odor neutralizing agent selected to neutralize the at least one odor.

15. The method of claim 14, wherein the at least one function includes controlling a concentration level of the at least one scent distributed.

16. The method of claim 14, further comprising instructing a plurality of drones to distribute a scent gradient of the at least one scent such that a first drone distributes a minimum value of the at least one scent and each subsequent drone distributes an increased amount of the at least one scent until a maximum value of the at least one scent is distributed.

17. The method of claim 13, wherein sampling the ambient air includes estimating an odor gradient associated with the at least one odor over a period of time.

18. A non-transitory computer readable storage medium comprising a computer readable program for air sampling using an unmanned aerial vehicle, wherein the computer readable program, when executed on a computer, causes the computer to execute:
sampling ambient air in at least one location to detect at least one odor;
identifying, using a database, the at least one odor, wherein the at least one odor is compared to identification information stored in the database;
identifying a source of the at least one odor using pattern recognition;
estimating an assessment value associated with the at least one odor, the assessment value including a hedonic assessment scaling the at least one odor on a perceptual axis reflecting a level of odorant pleasantness; and
automatically distributing at least one scent selected to impact the at least one odor when the assessment value exceeds a predetermined threshold on a hedonic scale.

19. The non-transitory computer readable storage medium of claim 18, wherein distributing at least one scent includes distributing an odor neutralizing agent selected to neutralize the at least one odor.

20. The non-transitory computer readable storage medium of claim 19, further comprising instructing a plurality of drones to distribute a scent gradient of the at least one scent such that a first drone distributes a minimum value of the at least one scent and each subsequent drone distributes an increased amount of the at least one scent until a maximum value of the at least one scent is distributed.

* * * * *